United States Patent [19]
Bigazzi

[11] Patent Number: 5,952,296
[45] Date of Patent: Sep. 14, 1999

[54] METHOD OF USING RELAXIN AS THERAPEUTIC OR PREVENTING AGENT

[76] Inventor: Mario Bigazzi, Via del Palmerino No.11, Florence, Italy, 50137

[21] Appl. No.: 08/403,878
[22] PCT Filed: Jul. 26, 1994
[86] PCT No.: PCT/IT94/00124
 § 371 Date: Mar. 23, 1995
 § 102(e) Date: Mar. 23, 1995
[87] PCT Pub. No.: WO95/03822
 PCT Pub. Date: Feb. 9, 1995

[30] Foreign Application Priority Data

| Jul. 27, 1993 | [IT] | Italy | FI93A0143 |
| Feb. 19, 1994 | [IT] | Italy | FI94A0036 |
| Feb. 25, 1994 | [IT] | Italy | FI94A0039 |

[51] Int. Cl.$^6$ ................................................. A61K 38/00
[52] U.S. Cl. ......................... 514/3; 514/12; 514/822; 514/885
[58] Field of Search ...................... 514/3, 12, 822, 514/885

[56] References Cited

U.S. PATENT DOCUMENTS

| 5,166,191 | 11/1992 | Cronin et al. | 514/12 |
| 5,656,592 | 8/1997 | Seed et al. | 514/12 |

FOREIGN PATENT DOCUMENTS

| 9303755 | 3/1993 | WIPO . |
| 9520395 | 8/1995 | WIPO . |

OTHER PUBLICATIONS

H Caplus AN: 1985: 554413, St. Louis et al., *Life Science*, 37(14), pp. 1351–1357, 1985.
Casten et al., *Angiology*, 11, pp. 408–414, 1960.
Medline AN: 93381427, Weisinger et al., *J. Endocrinol.*, 137(3), pp. 505–510. (abstract), Jun. 1993.
Relaxim—Procedings of a Workshop . . . , ed Boyant––Greenwood, Niall ad Greenwood, Elsevier 1981, pp. 1–134.
Chem Abstracts: vol. 103 (1985), 103:154413u.
Bani et al. Z–Mikrosk–Anat. Forsch(Leipz) 101(4) 1987, 577–96. Abstract.
Massicotte et al., Pros. Soc. Exp. Biol. Med (1989 Mar.) 190(3), 254–9. Abstract.
Bigazzi et al., Acta. Endocrinol (1986 Jun.) 112(2), 296–9, Abstract.
Weisinger et al., J. Endocrinology, vol. 137(3) (1993) pp. 505–510. Abstract.
Sanborn, B.M., Comp. Biochem Comp. Physiol. C. Comp. Pharm. Toxicol. 93(2) 1989, pp. 341–344. Abstract.
Osheroff et al., PNAS, vol. 89 (1992) pp. 2384–2388.
Miller et al. Am. J. Physiol. vol. 257(4) 26/4 (1989), H1127–H1131, Abstract.
Proceedings of the Australasian Society of Clinical ad Experimental Pharmacologies ad Toxicologish 1991. Abstract No. 117.
Domestic Animal Endocrinology. vol. 9, No. 1, Jan. 1992, McKinley et al. pp. 1–11.
Chem Abstract vol. 96 (1982):96;174647p.
Hall et al., Biol Reprod. vol. 42 (5–6) 1990, 769–74. Abstract.
R.X. Sands, The Canadian Medical Journal, vol. 78(12), Jun. 15, 1958, pp. 935–940.
A. Barousse, Medicina, vol. 38(2) Mar.–Apr.(1978) pp. 215–216. No Translation.
Caster et al. Angiology vol. 11 (1960) pp. 408–414.
Osherhoff and Ho, J. Biol. Chem., vol. 265(20), Jul. 16, 1993, pp. 15193–15199.

*Primary Examiner*—Cecilia J. Tsang
*Assistant Examiner*—C. Delacroix-Muirheid
*Attorney, Agent, or Firm*—McGlew and Tuttle, P.C.

[57] ABSTRACT

Methods of using relaxin (RLX), a peptide hormone of the insulin family, which has been found to produce effects on the walls of blood vessels, on blood clotting and on blood lipids and electrolytes, per se, and through the stimulation of the synthesis and release of the two powerful substances: nitric oxide (NO) and atrial natriuretic peptide (ANP), are contemplated whereby RLX is administered to a patient for increasing blood flow, producing dilation of the arteries, influencing blood clotting and fibrinolysis, reducing blood lipids, inducing reduction of blood osmolarity and sodium concentration, and through NO for inhibiting release of histamine from mast cells. RLX is accordingly used as a therapeutic agent in methods for treating arteriosclerosis and vascular diseases, ischemia and thrombosis, hypertension and pregnancy's gestosis, and other diseases, or allergic and inflammatory disorders as dysfunctions in fluid and electrolyte balance.

37 Claims, 5 Drawing Sheets

RLX – BLOOD VESSELS

METHOD OF USING RELAXIN AS THERAPEUTIC OR PREVENTING AGENT

FIELD OF THE INVENTION

The invention relates to methods of using relaxin (RLX) as a pharmaceutical agent for the treatment of particular disease.

Relaxin is a hormone secreted by the ovaries especially during pregnancy. Its structure is very similar to insulin and it is different for each species of animals. Its known activities are linked to reproduction and specifically to pregnancy and delivery. This hormone is recognized as being capable of inhibiting spontaneous contractions of the uterus during pregnancy and of provoking the enlargement of the pubic symphysis and cervix at delivery time.

BACKGROUND ART

The availability of pure preparations of relaxin has always been quite limited due to the difficulty of isolating and purifying it, as well as to the scarcity of organs from which to extract it (Bryant Greenwood G. D., Endocrine Review, 3-62-1982). These limitations and the difficulties in preserving the biological activity of the hormone produced a progressive lack of interest until an almost complete oblivion of relaxin, and finally even the disbelief in relaxin existence.

The purification and sequentiation of relaxin and its production by genetic engineering, obtained from 1974 to 1983, offered new possibilities to finally research and understand the biology and the role of this hormone. In this respect see Sherwood et al., Arch. Biochem. Biophys. 160-185-1974; James et al., Nature 267, 554, 1974; Hudson et al., Nature, 301, 628, 1983; Bigazzi M. et al, Biology of Relaxin and its role in the human, International Congress Series 610, Excerpta Medica-Amsterdam-1993.

Actually, there is a bulk of evidence that RLX is a multifunctional hormone, efficacious on reproductive organs, mammary glands and connective tissues, but so far no clinical use has been realized.

A new possible target for RLX could be the cardiovascular system. The cardiovascular system can be divided into three different main sections:

the heart represents the pump of the system, the blood vessels represent the circulation pipes, the blood circulates in the vessels and contributes in a positive or negative way to circulation through the hemostatic system and through the concentration of various substances such as lipids, electrolytes, water and the like.

Some diseases or dysfunctions of the cardiovascular system can occur separately only in one of these main sections without affecting directly the others (such as the contractile failure and rhythm disturbances of the heart, some congenital abnormalities of the vessels or alterations in the hemostatic chain as thrombophilic or hemophilic diseases etc.).

Some of the more frequent circulatory diseases can begin in one section but involve soon also other parts of the system. This is the case of arteriosclerosis in which both the alterations of the blood composition and of the arterial walls are responsible for the pathogenesis and clinical features of the disease.

The circulatory disease which derives from arteriosclerotic processes represents one of the major problems of mankind. In fact it is the most frequent cause of death, at least in 4% of the population (especially from myocardial or cerebral infarction). This explains the great interest of researchers in this field.

Presently many different pharmacological tools are known and used to correct the thrombo-ischemic diseases of circulation, separately aimed at vessel dilation or blood clotting correction, clot dissolution, blood lipid reduction and so on.

The effects of RLX on the heart were discovered in 1990 by Osheroff et al., see Osheroff PL et al., Proc. Natl. Acad. Sci. USA; 1992.89: 2384–2388; and U.S. Pat. No. 5,166,191.

They described the binding of RLX to heart atria and an increase of the rhythm and contractions of the in vitro isolated atria. From these experiments they hypothesized a possible role of RLX in dysfunctions of heart rhythm and in diseases concerning heart contraction, such as congestive heart failure.

Some observations have been done on circulation. It has been noted that the Raynaud's lesions completely disappear during early pregnancy. Early clinical studies made by Casten and Allon in 1958 and 1960 with ovine preparation of RLX of poor purity and uncertain biological activity have shown that it was beneficial in healing Raynaud's lesions arising from obliterative peripheral arterial diseases but the treatment involved use of RLX in combination with small amounts of exogenous estrogen (see Casten G. G. et al., Angiology 11, 408, 1960).

In 1986 it has been reported that local application of porcine RLX to mesocaecum of male rats produces dilation of venulae and antagonizes the vasoconstrictive effects of norepinephrine and promethazine (see: Bigazzi M et al., Acta Endocrinol. 112–296, 1986).

In 1989 Massicotte et al. reported that a two days infusion of rat RLX blunted the vasoconstrictive effects of norepinephrine and vasopressin on mesenteric artery of spontaneously hypertensive rats (see: Massicotte et al.: Proc. Soc. Exp. Biol. Med.:190, 254, 1989).

However, the physiological significance of these observations remained obscure and up to now it was not known whether or not RLX influences the circulatory system.

No effects of RLX have been reported so far on the hemostasis and blood composition.

SUMMARY OF THE INVENTION

The evidence has now been reached that RLX is a fully active hormone in the blood vessels, in the hemostatic processes and in blood composition and may therefore be used in methods for the treatment of the thrombo-ischemic or circulatory diseases.

In fact, it has now been surprisingly discovered and experimentally verified that this hormone can act as a factor of full protection against arteriosclerosis and ischemic or thrombotic pathologies. As a matter of fact RLX induces dilation of blood vessels' smooth muscle cells which results in an increment of blood flow; inhibits coagulation processes, intensifies the fibrinolysis and lowers blood concentration of lipids and sodium. It has been recognized that RLX elicits this wide spectrum of effects directly and through release of two important substances, Nitric Oxide (NO) and Atrial Natriuretic Peptide (ANP), which largely contribute to the above mentioned results on vessel walls and blood components.

Finally, the stimulation of NO and ANP release allows RLX to influence functions in organs other than the circulatory system, such as the release of histamine from mast-cells and water and sodium diuresis from the kidneys.

Therefore, this invention relates to the use of RLX for production of medicaments and methods for the treatment and prevention of two important circulatory diseases which could be classified as follows:

A) Arteriosclerotic cardio-vascular diseases, ischemic and thrombotic pathologies;

B) Preeclampsia-eclampsia and gestosis of pregnancy.

Furthermore, diseases influenced by histamine release and ANP secretion can also be treated or prevented by means of RLX in view of its effect on the stimulation of NO and ANP release.

BRIEF DESCRIPTION OF THE DRAWINGS

The results of experimentation on use of RLX in the treatment of these diseases will be discussed in detail hereinafter, reference being made also to the accompanying drawings, reporting experimental results i.e. using RLX in the absence of attendant exogenous estrogenic hormone (cf. Casten G. G. et al., Angiology, supra). In particular.

DETAILED DESCRIPTION OF THE INVENTION

A. Arteriosclerotic Cardio-vascular Diseases, Ischemic and Thrombotic Pathologies and Hypertension According to a first aspect of the present invention, the use of RLX for pharmaceutical formulations is foreseen, which are:

destined to induce vascular dilation of cardiac and other organs' arteries, aimed to correct alterations of vascular functions in human organs, as cavernous bodies of the penis, aimed to control thrombotic diseases, aimed to inhibit the formation of clots and/or to provoke their dissolution, aimed to reduce the number and aggregation of circulating platelets, aimed to inhibit the formation of platelets from megacariocytes, destined to reduce circulating fibrinogen, destined to increase fibrinolysis, destined to reduce blood lipids concentration, aimed to prevent or to treat arteriosclerosis, aimed to stimulate ANP secretion from heart atrial myocytes, aimed to stimulate water and sodium secretion from kidneys, aimed to correct edema and excess of water retention, aimed to ameliorate lymphoedema, destined to reduce the volume of circulating blood in congestive heart failure;

aimed to treat obliterative or obstructive peripheral arteriopathy, such as constrictive or spastic arteriopathy.

In order to develop the described concepts the following experimental models have been performed:

1. Studies on blood vessels:
   a. on coronary system,
   b. on bovine aorta smooth muscle cells in vitro,
   c. on the circulation of the penis,
2. Studies on hemostatis:
   a. platelets.
   b. humoral factors.
3. Studies on ANP
   a. Electron microscopic studies and determination of ANP in atrial myocytes.
   b. on blood osmolarity and Na concentration.

The results of the experiments are set forth hereinafter.

1—STUDIES ON BLOOD VESSELS

The results of the studies on the effect of RLX on blood vessels show that the peptide acts on the circulatory system at different levels.

Figure 1A:
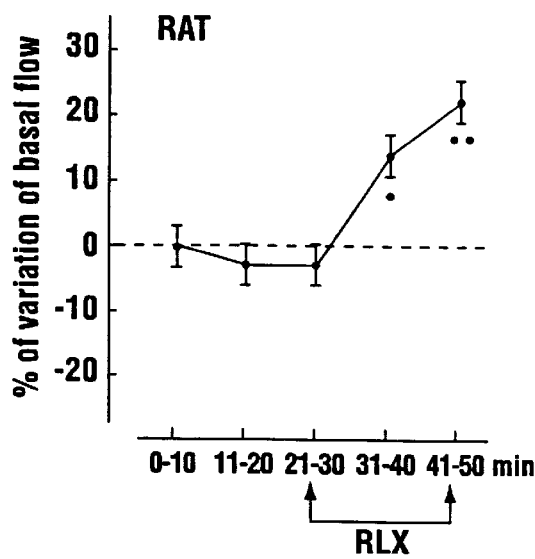
FIG. 1A and B show the effect of RLX on coronary flow determined by experiments on rats (diagram A) and on guinea pigs (diagram B)
Figure 1B:
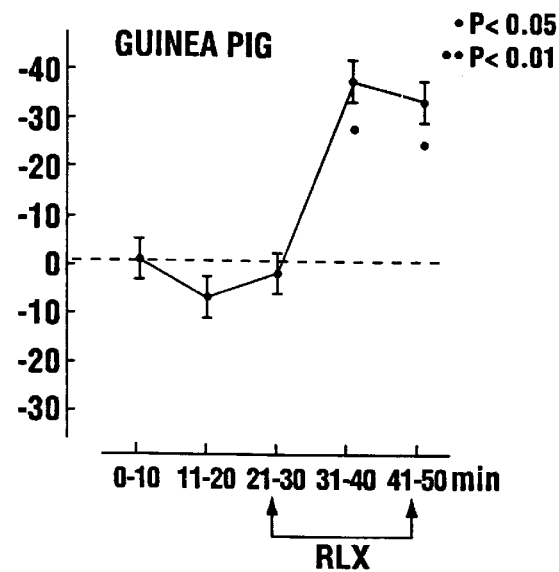

1-a The coronary system was deemed a suitable model for studying the influence of RLX on dilation of blood vessels. Rat and guinea pig hearts, isolated and perfused in vitro in a Langendorff apparatus, were used to evaluate whether RLX causes changes in the coronary flow. After 30 minutes stabilization, in some experiments RLX (30 ng/ml) was added to the perfusion fluid and perfusion lasted for 20 minutes. In other experiments, RLX (30 ng/ml) was injected as a bolus into the aortic cannula. The perfusates were collected and the coronary flow determined. The results obtained indicate that RLX increases significantly the coronary flow. FIG. 1 shows two diagrams (A and B) relevant to experiments on rats and guinea pigs respectively. The percentage of basal flow variation is depicted versus time. In these diagrams (as well as in the next ones) values are expressed as mean ± SE (standard error). Statistic analyses were done calculating the Student's test (P), whose value is shown in the diagrams.

Figure 2A:
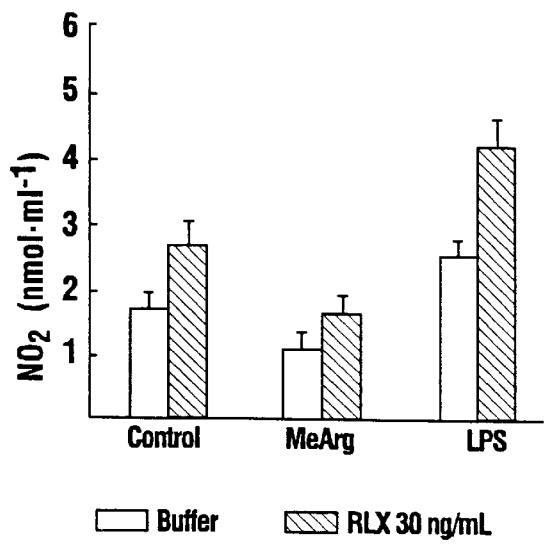
FIG. 2A and B show the effect of RLX on coronary flow (diagram A) and NO release (diagram B) respectively in the presence of NO-synthase, inhibitors and NO-synthase inducer.
Figure 2B:
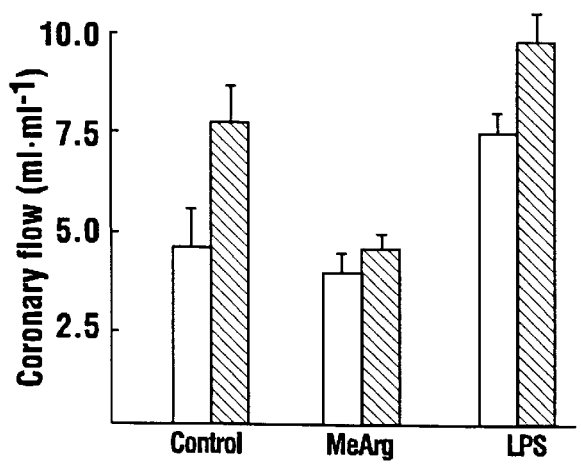

To clarify the mechanisms of action of RLX on dilation of coronary vessels, nitric oxide (NO) production and histamine release were assayed in the perfused guinea pig hearts. NO, which is known to be a powerful vasodilatory agent, was measured by determination of nitrites (stable end-products of NO metabolism) in the perfusates. In some experiments, $N^W$-monomethyl L-arginine (MeArg), a NO-synthase inhibitor, was added to the perfusion fluid before giving RLX as a bolus; in other experiments, guinea pigs were pretreated with E.coli lipopolysaccharide (LPS), an inducer of NO-synthase activity before heart isolation and perfusion. The results obtained show that RLX causes a significant increase in the nitrite amounts in the perfusates (two-fold increase over the basal value), indicating enhanced NO production. This was further confirmed by the experiments with MeArg and LPS, drugs that blunted and enhanced the RLX-induced increase in the coronary flow, respectively (FIG. 2). Coincidentally with the nitrite increase, the amount of histamine in the perfusates was significantly reduced by RLX.

In conclusion, RLX can be regarded as an agent capable of improving myocardial perfusion through activation of the L-arginine pathway.

NO is produced by different components of the vascular wall, i.e. endothelial cells and smooth muscle cells, as well as by perivascular mast cells (see Iadecola C., TINS, 16:206, 1993; Mellion B. T. et al., Blood, 57:946, 1981; Radomski M. V. et al., Biochem. Biophys. Res. Commun., 148:1482, 1987). It is also known that NO plays a major role in the regulation of the vascular tone through a cGMP-dependent mechanism, which results in a reduction of cytosolic $Ca^{2+}$, myosin dephosphorylation, and finally smooth muscle cell relaxation (see Noriyuki H. et al, Am. J. Obstet. Gynecol. 159: 27–31, 1988).

1-b Smooth muscle cells of the vascular wall obtained from bovine aorta (BASM) and cultured in vitro are a suitable in vitro model for understanding the mode of action of RLX on blood vessels. The results of the immunocytochemical studies carried out with anti-actin antibodies on BASM cells incubated for 4 hours with 100 ng/mL RLX showed that the peptide induces changes in the actin cytoskeleton, consistent with cell flattening, as occurs during relaxation in vivo.

Figure 3:
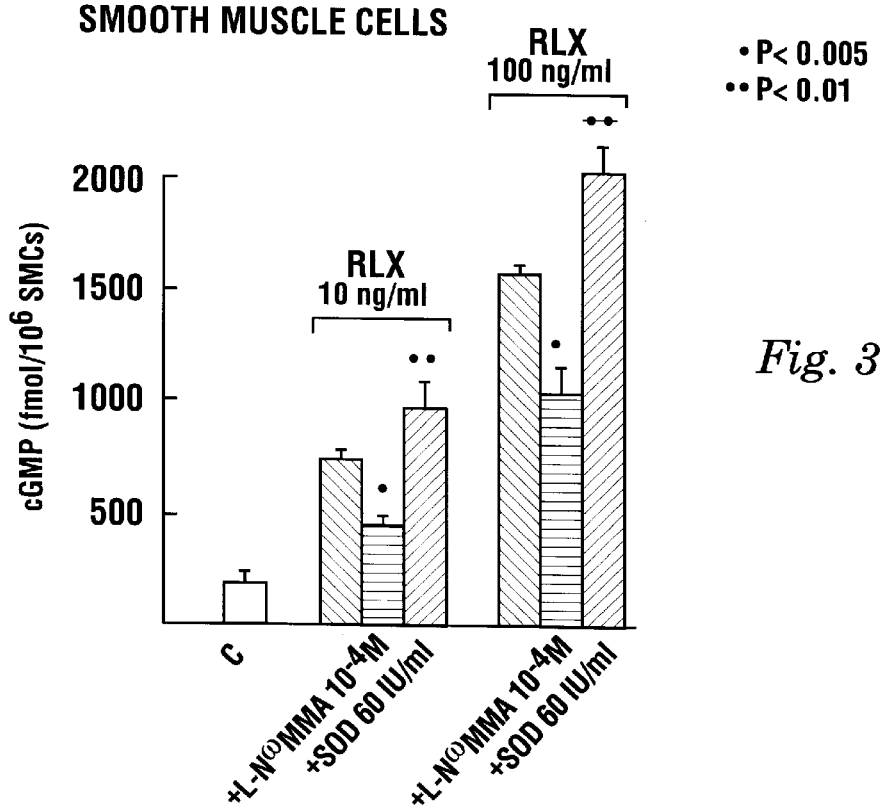
FIG. 3 shows the effect of RLX on cGMP level on smooth muscle cells of the vascular wall obtained from bovine aorta cultured in vitro.

To clarify the mechanisms of action of RLX on BASM cells, the peptide was added to the culture media at concentrations of 10 and 100 ng/mL for 1 hour and the intracellular cGMP levels evaluated. RLX caused a striking concentration-related increase in intracellular cGMP levels (400% and 900% over the values of the untreated cultures). Moreover, pretreatment of the cells with MeArg, that inhibits NO-syntase, and superoxide dismutase (SOD), which potentiates NO activity, led to depression or enhancement of the RLX-induced increase in cGMP, respectively, thus indicating that the rise in cGMP is due, at least in part, to an enhancement of NO production. These results are summarized in the diagrams of FIG. 3.

Figures 4A, 4B:
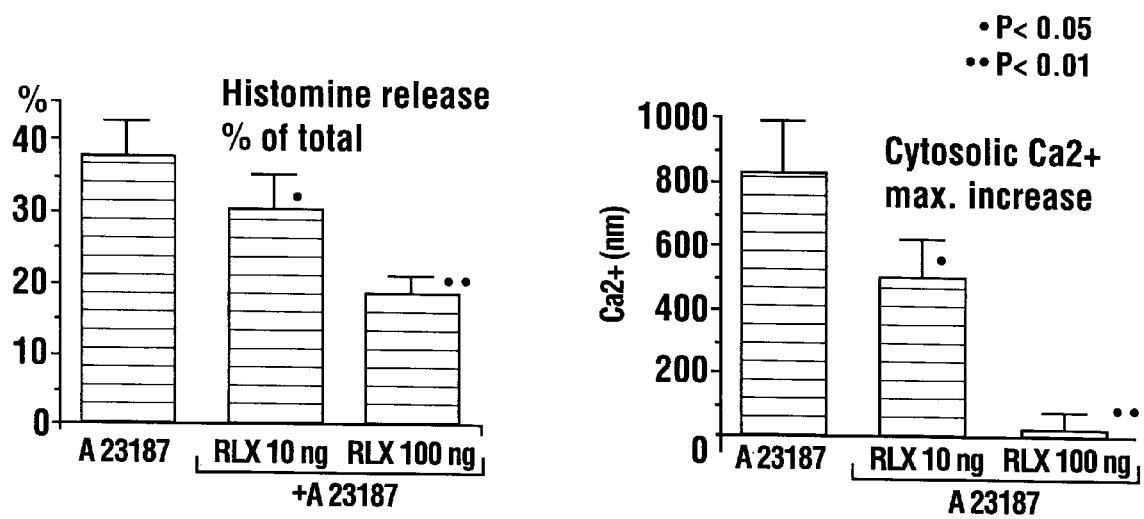
FIG. 4A and B show the effect of RLX on histamine release (diagram A) and cytosolic $Ca^{2+}$ release (diagram B) on mast cells in vitro.

1-c Mast cells (MCs) are known to produce and release vasoactive substances. It has therefore been investigated whether RLX also exerts its vasodilatory action by influencing MC function. The results of the experiments on isolated serosal rat and guinea pig MCs and on rat mesenteric MCs in vivo showed that RLX inhibits calcium-ionophore-induced and anaphylactic histamine release, as well as MC degranulation. This effect is mediated by a stimulation of NO production. In fact, the RLX-induced depression of histamine release evoked by calcium ionophore was prevented by MeArg and potentiated by SOD. Moreover, RLX blunted the rise in the intracellular $Ca^{2+}$ levels evoked by calcium ionophore in a concentration-related fashion (41% decrease with 10 ng/mL RLX and 97% decrease with 100 ng/mL RLX). From these findings, it emerges that the vasodilatory action of RLX is not due to histamine release by MCs but, rather, to production of the vasodilatory agent NO, in keeping with its effect in the coronary system. The above results are summarized in the diagrams A and B in FIG. 4.

Figure 5A:
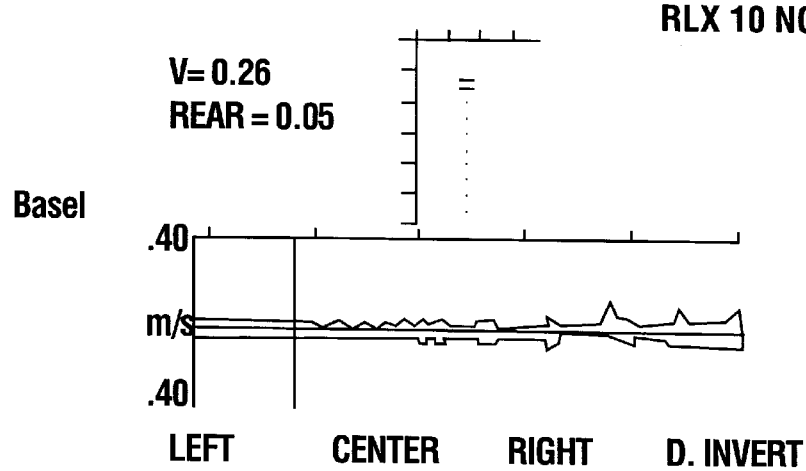
FIGS. 5A–5C show the effect of RLX on blood flow in the human penis.
Figure 5B:
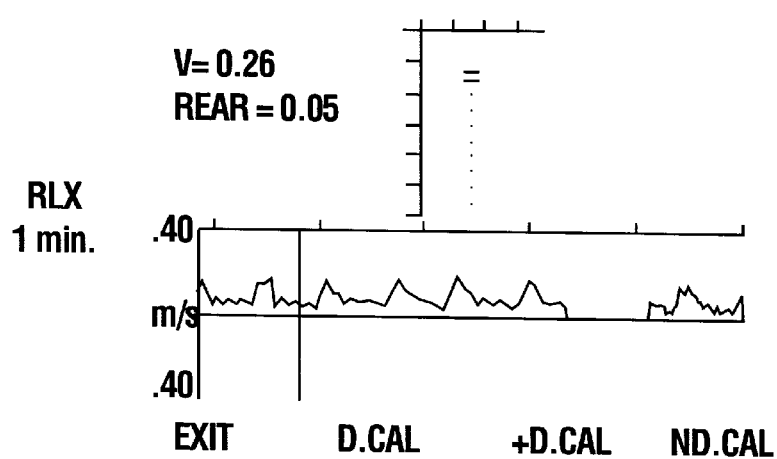
Figure 5C:
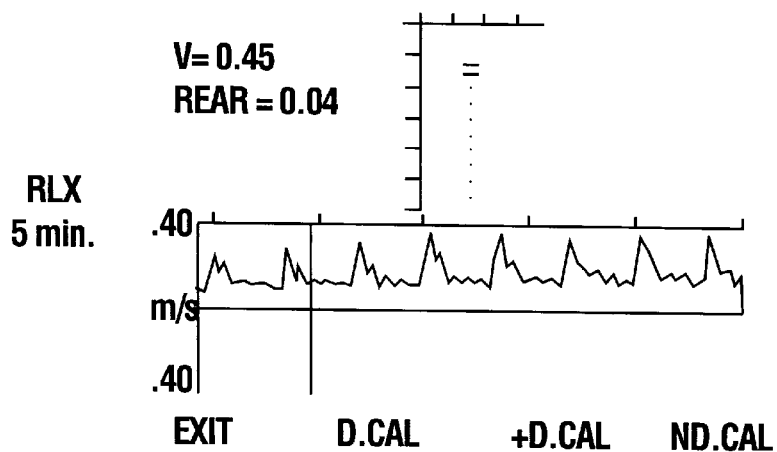

1-d The blood flow in the penis is influenced by local NO production. Based on the ability of RLX to stimulate NO synthesis, the effect of the peptide on the blood flow in the deep artery of the penis was investigated. RLX (sterilized by microfiltration) was injected into the cavernous bodies of 4 human normal volunteers at a dose of 10 ng, and the blood flow measured by an echo-doppler Acuson 128, 1–6 minutes after the injection. In all the subjects, RLX caused a striking increase in the blood flow, as compared with basal flow evaluated before injection. In two subjects erection was also observed 5–10 min. after RLX injection. In FIG. 5 the echo-doppler images are reported, showing the flow under normal conditions (diagram A), 1 min. after RLX injection (diagram B) and 5 min. after RLX injection (diagram C).

2—Studies on Hemostasis

Starting from the finding that RLX enhances NO production in several components of the cardiovascular system, and based on the well-known ability of NO in inhibiting platelet adhesion and aggregation, a possible role of RLX has been searched for in hemostasis by studying platelets and plasma factors of hemostasis.

A first series of experiments was carried out on isolated platelets from human volunteers and rabbits, incubated with RLX and then stimulated with proaggregants.

A second series of experiments was performed in male rats injected intraperitoneally with RLX and sacrificed 20 minutes later. Before sacrifice, blood and plasma samples were collected for studying plasma hemostasis factors and number of circulating platelets; upon sacrifice, spleen specimens were taken for studying the morphology of megacaryocytes. The results of these studies show that RLX is capable of influencing hemostasis by acting on both platelets and plasma soluble factors.

2-a Platelets

Figure 6:
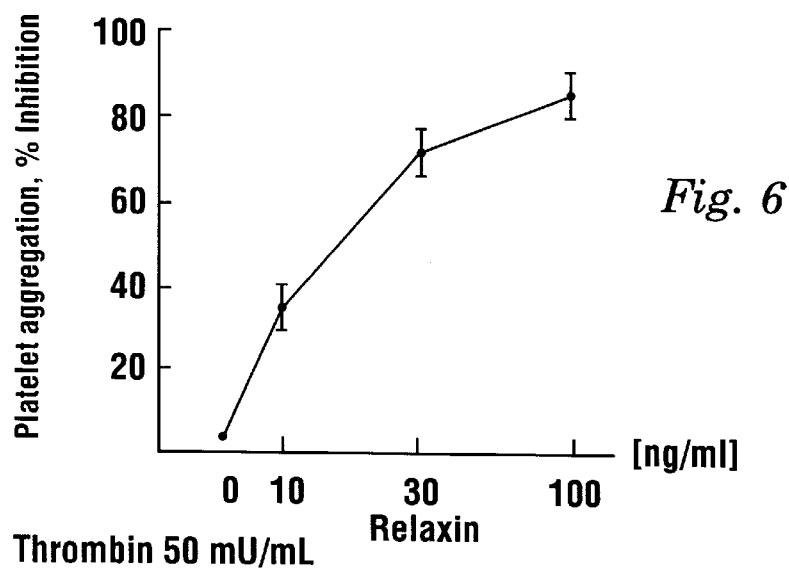
FIG. 6 is a diagram showing the effect of RLX on platelet aggregation inhibition.
Figure 7:
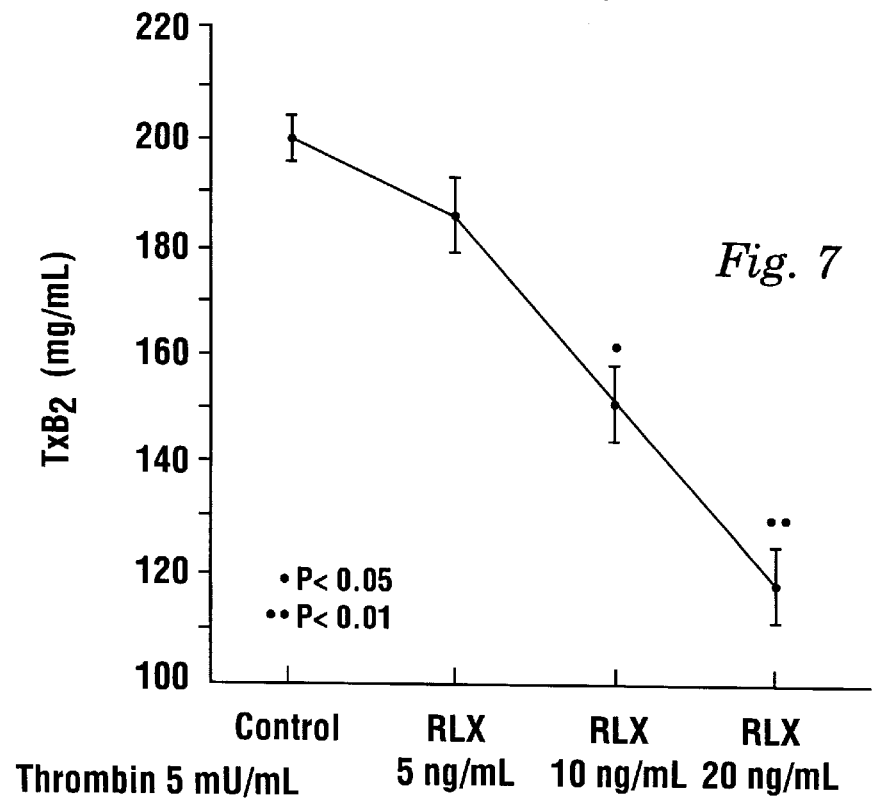
FIG. 7 shows the effect of RLX on inhibition of thromboxane production.
Figure 8:
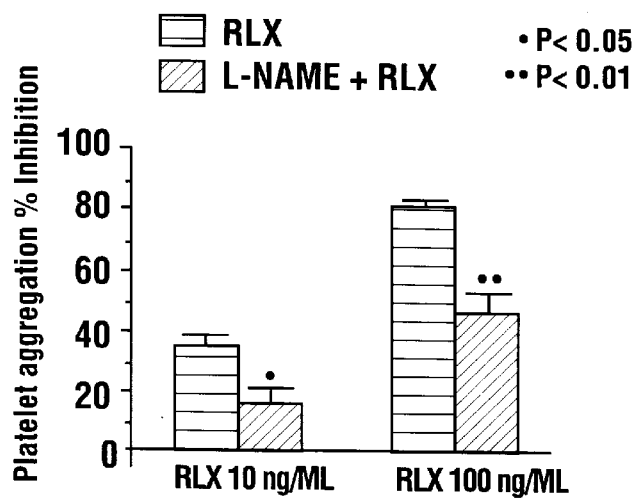
FIG. 8 shows the effect of RLX on NO production.
Figure 9:
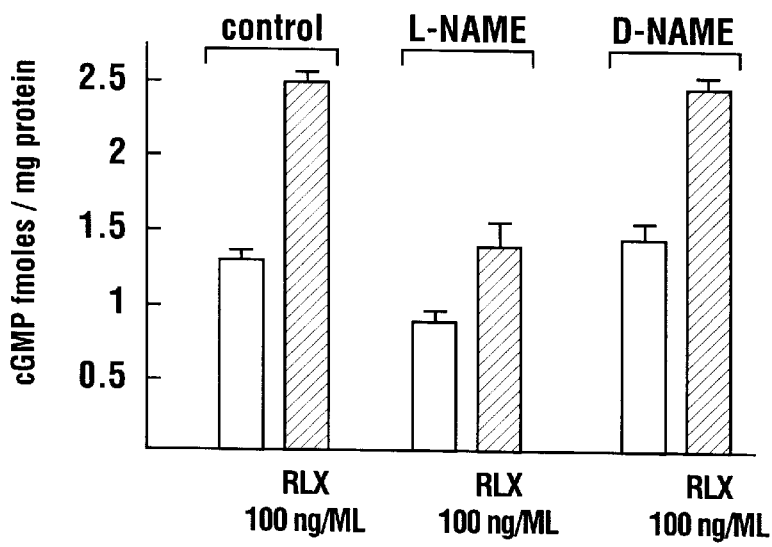
FIGS. 9 and 10 show the correlation between the platelet aggregation inhibition of RLX and its effect on cGMP and cytosolic $Ca^{2+}$ production respectively.
Figure 10:
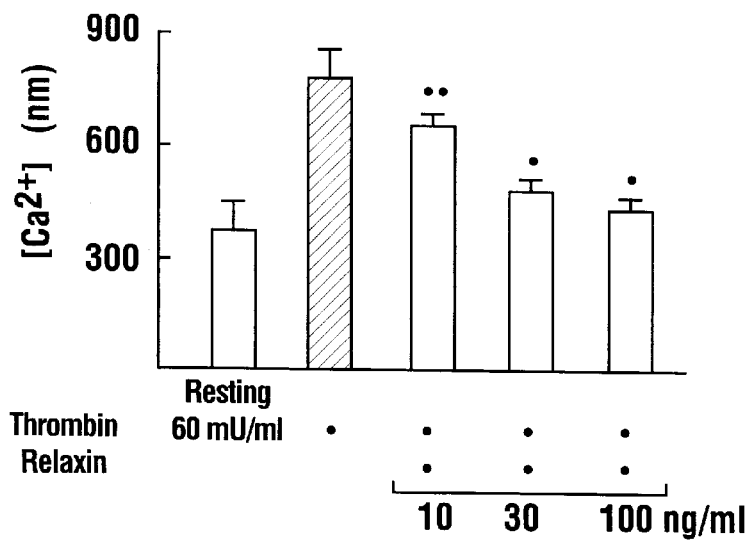

The peptide has been shown to depress markedly platelet aggregation induced by different proaggregants (FIG. 6). This effect was concentration-related and attained a maximum of 80% inhibition with 100 ng/mL RLX. The inhibitory action of RLX on platelet aggregation is exerted by both an inhibition of thromboxane production and a stimulation of endogenous NO synthesis. This can be seen from the diagrams of FIGS. 7 and 8 respectively, and involves subsequently a rise in intracellular cGMP (as shown in FIG. 9) and a decrease of cytosolic $Ca^{2+}$ (as shown in FIG. 10), which ultimately leads to a powerful inhibition of platelet aggregation.

Ultrastructural examination of the platelets indicates that RLX hinders the conformational modifications and granule exocytosis that occur during aggregation, thus fitting closely with the functional data. The findings obtained from the in vivo experiments in rats show that RLX causes a reduction in the number of circulating platelets. This may be a consequence of a depression of platelet release by megacaryocytes. In fact, the ultrastructural findings suggest that RLX hinders proplatelets and demarcation membrane vesicles to coalesce and fuse with the plasma membrane, so that platelets cannot be released from the cell surface.

2-b Humoral factors

Besides its effects on platelets, RLX also causes a significant, concentration-dependant increase in the plasma levels of tPA and PAI-1, that are known to be factors of endothelial origin involved in fibrinolysis, and a slight decrease in some coagulation factors such as fibrinogen and prothrombin fragments F1+2. Therefore, the peptide also promotes fibrinolysis, probably by acting on endothelium. The effect of RLX on these plasma factors is shown in Table I, the data relating to experiments on rats.

TABLE I

| Plasma Factors (rat) | RLX - HEMOSTASIS | |
| --- | --- | --- |
| | Controls | RLX-Treated |
| Fibrinogen (mg/dl) | 212 ± 16 | 185 ± 26 |
| tPA Ag (ng/mL) | 0.31 ± 0.1 | 0.52 ± 0.1 |
| tPA activity (U/mL) | 0.12 ± 0.01 | 0.37 ± 0.03*** |
| PAI-1 Ag (mg/mL) | 8.9 ± 1 | 12.8 ± 0.9** |
| PAI-1 activity (U/mL) | 8.16 ± 1.3 | 11.7 ± 0.7* |
| PT (sec.) | 14.4 ± 0.5 | 15.1 ± 0.5 |

TABLE I-continued

RLX - HEMOSTASIS

| Plasma Factors (rat) | Controls | RLX-Treated |
|---|---|---|
| aPTT (sec.) | 19 ± 0.8 | 19 ± 2.5 |
| F 1 + 2 (nM/mL) | 0.034 ± 0.01 | 0.028 ± 0.01 |

*P < 0.05
**P < 0.01
***P < 0.001

3-c Lipids blood concentration

The assays of cholesterol and triglycerides on the peripheral blood serum shows that RLX administration produces a striking decrease of their concentration up to 38 and 55% reduction, respectively.

3—Studies on ANP Secretion 3-a ANP secretion was studied in rats following intraperitoneal administration of 10 μg RLX. It is known that atrial myocardiocytes have an endocrine function, being able to synthesize and release a peptide, called atrial natriuretic peptide (ANP) that, besides its firstly recognized effect in stimulating natriuresis, has other properties such as a negative action on blood pressure due to a decrease in the vascular tone and a shift of the plasma fluid in the interstitial compartment.

A possible relationship has therefore been searched for between RLX and ANP by evaluating the amount of immunoreactive ANP and the ultrastructural features of atrial myocardiocytes of rats upon RLX treatment. Twenty minutes after administration of the peptide, the amount of immunoreactive ANP was strongly decreased, as well as the number of ANP-storing granules. No appreciable changes were found in the extension of the ergastoplasm and Golgi apparatus. This suggests that RLX promotes release of ANP rather than inhibiting its synthesis. Determinations of ANP content in rat atria homogenates by RIA before and after in vivo administration of RLX are in agreement with the EM findings.

3-b Blood osmolality and Sodium concentrations were measured to prove the effect of ANP secretion through its effects on kidneys and on peripherical blood. In the rats of the above mentioned experiments RLX was proved to reduce the plasma osmolality of 8.5 milliosmoles per kg. body weight, and the sodium concentration from 142±4 to 136±2 mEq/1.

Advantages

From the above it is seen that RLX is effective on the cardiocirculatory system at different levels and that a common mechanism of action involving the L-arginine NO pathway and intracellular cGMP and $Ca^{2+}$ underlies most of the observed responses. This allows for RLX to be regarded as a novel agent capable of favouring myocardial perfusion, blood supply to organs and fibrinolysis, and of depressing platelet activity and coagulation, as well as lipid blood concentrations, which are all involved in the pathogenesis of arteriosclerotic lesions. Therefore RLX may be used in prevention and/or therapy of ischemia-derived, allergic, hypertensive and thromboembolic disorders and arteriosclerosis.

The above mentioned findings prove that RLX can also be involved in the control and therapy of diseases of systems different from the circulatory apparatus through the stimulation of production of NO and secretion of ANP.

B- pre-eclampsia, eclampsia and gestosis of pregnancy

Normal course of pregnancy is dependent on the deep organic changes it self-induces in the pregnant woman. Shorlty after delivery normality is resumed.

One of the most surprising phenomena involves the hydrosaline balance and typically occurs in the first weeks of pregnancy: the renal function, the vascular system and hemostasis all undergo a new arrangement.

1) Renal function and hydro-balance:

The arterial flow of the kidney and glomerular filtration are increased. Sodium excretion is increased while its reabsorption is decreased. The result of it is a decreased plasmatic concentration of sodium ion and an increased concentration of potassium ion. That implies an important drop in the osmolar pressure of plasma whose values reach as much as 10 milliosmole per kg of body weight lower than normal values in male and non-pregnant female.

2) Vascular system:

There is evidence of lower peripheral resistence due to dilation of arterioles and of the increase of the interstitial liquid as a consequence of dilation and increased permeability of the capillary bed.

3) Hemostasis:

Coagulation factors are increased in peripheral circulating and in placental blood; nevertheless there is no occurrence of intravascular coagulation during pregnancy.

The physiology of the particular cardio-vascular and hydro-electrolytic situation characteristic of pregnancy remains obscure. Its identification would be of paramount theoretical and practical importance since it would show how to intervene with corrective measures into the serious pathological situations observed when, during pregnancy, the above balance is disturbed.

Gestosis, pre-eclampsia and eclampsia all endanger the course of pregnancy and can cause vascular irreversible damage to the fetus and the mother. Various hormonal hypotheses have been proposed but the hormone or the combination of hormones responsible for such a particular situation were never identified.

The effects of RLX set forth hereinabove, on the circulatory system and on ANP secretion point to the conclusion that this may be the very hormone responsible for the whole phenomena observed during pregnancy.

In fact relaxin was shown to be active:
- on the vascular system; inducing hypotension by vasodilation of arterioles and capillaries and increasing tissue imbibition both by its own direct effect and indirectly by inducing ANP secretion.
- on the hydrosaline balance and on the renal function, again inducing ANP release and therefore promoting loss of Na and decrease of plasmatic osmolarity.
- on the hemostasis; by reducing platelet aggregation, by reducing fibrinogen concentration and by increasing fibrinolysis.

It is therefore postulated that the absence or deficiency of relaxin would be the cause of hypertension, electrolytic imbalance with increased retention of Na, edema and intravascular thrombosis that are the three pathogenic events of the gestosic syndrome.

It is therefore claimed that relaxin is a pharmaceutical substance or the first of a line of pharmaceutical substances, suitable to be used for the treatment of pathologic pregnancy complications like: hypertension, electrolytic imbalance with sodium retention, intravasal or intraplacental coagulation and eclamptic syndrome.

C) Diseases influenced by histamine release (allergic and phlogistic diseases) and ANP secretion.

During the studies on the circulatory system a new unreported biological activity of relaxin was discovered: the hormone shows itself to be able to inhibit or, depending on the dose, totally suppress, the secretion of histamine by the mastocytes and the secretion of ANP from the atriocytes.

The invention therefore also relates to the use of relaxin for the treatment of pathological situations due to histamine liberation like allergic and inflammatory diseases and disorders of fluid and electrolytes balance.

More in detail, according to the invention, the use of pharmaceutical preparations containing relaxin is indicated for:

the treatment of allergic diseases like allergic rhinitis, bronchial asthma, etc.

the treatment of anaphylactic accidents, idiosyncrasy to drugs, etc.

the control of tissular reactivity, swellings, urticaria, etc.

relieving or blocking inflammations sustained by histamine liberation.

The experimental models used to develop the above concepts and the results that were obtained were ascertained on the previously discussed studies on blood vessels and ANP secretion.

In all the experiences performed relaxin has shown no effect whatsoever on the basal liberation of histamine by mastocytes. On the contrary it has shown to be capable of greatly inhibiting histamine secretion in cells having been chemically stimulated by the ionophore or sensitized by the allergen in both experimental conditions. The degree of inhibition was the function of the dose of relaxin being used.

The microscopic observation of the cells confirmed that in the presence of relaxin the mastocytes do not show release of histamine granuli which is usually induced by the ionophore and the allergen.

The results obtained are consistent with the observation that allergic diseases (sustained by histamine release) usually improve during pregnancy when relaxin is present in circulating blood They also justify the hypothesis that relaxin may be useful as a new drug, or the first of a new line of drugs, for the treatment of allergic, anaphylactic, inflammatory diseases, or diseases sustained by histamine liberation.

For the property of stimulating ANP secretion RLX can influence:

the disorders of water and sodium execretion from the kidneys.

the increase of water and sodium retention in tissues.

This allows one to foresee a possible use of RLX in the treatment of local or diffused edema, in hydrope, in lymphoedema, etc.

I claim:

1. Method of treating circulatory vascular ischemic disease involving constriction of the blood vessels, vascular dysfunction, or obliterative or obstructive peripheral arteriopathy in a human patient exhibiting said disease, comprising administering to said patient in the absence of attendant exogenous estrogenic hormone an effective amount of relaxin or derivative thereof for dilation of the blood vessels, for relieving said vascular dysfunction, or for relieving said obliterative or obstructive peripheral arteriopathy, for relieving said disease.

2. Method of claim 1 wherein the disease involves constriction of the blood vessels and the relaxin or derivative thereof is administered in an amount effective for dilation of the blood vessels.

3. Method of claim 1 wherein the disease involves vascular dysfunction and the relaxin or derivative thereof is administered in an amount effective for relieving said dysfunction.

4. Method of claim 3 wherein the disease involves vascular dysfunction of the cavernous bodies of the penis and the relaxin or derivative thereof is administered in an amount effective for relieving said dysfunction.

5. Method of claim 1 wherein the disease involves obliterative or obstructive peripheral arteriopathy and the relaxin or derivative thereof is administered in an amount effective for relieving said arteriopathy.

6. Method of claim 5 wherein the disease involves obliterative or obstructive peripheral arteriopathy comprising constrictive or spastic arteriopathy and the relaxin or derivative thereof is administered in an amount effective for relieving said arteriopathy.

7. Method of claim 1 wherein said amount is about 5, 10, 20, 30 or 100 ng/mL and the relaxin or derivative thereof is in sterilized purified form.

8. Method of treating circulatory thrombotic disease in a human patient exhibiting said disease, comprising administering to said patient in the absence of attendant exogenous estrogenic hormone an effective amount of relaxin or derivative thereof for relieving said disease.

9. Method of claim 8 wherein the disease involves blood coagulation and platelet aggregation and the relaxin or derivative thereof is administered in an amount effective for control of said blood coagulation and platelet aggregation.

10. Method of claim 8 wherein the disease involves platelet formation from megacariocytes and aggregation thereof and the relaxin or derivative thereof is administered in an amount effective for reducing and controlling said platelet formation and for inhibiting said aggregation thereof.

11. Method of claim 8 wherein the disease involves the formation of clots and the relaxin or derivative thereof is administered in an amount effective for inhibiting the formation of said clots.

12. Method of claim 8 wherein the disease involves increased blood concentration of circulating fibrinogen and the relaxin or derivative thereof is administered in an amount effective for reducing the blood concentration of circulating fibrinogen.

13. Method of claim 8 wherein the disease involves fibrin and clot formation and the relaxin or derivative thereof is administered in an amount effective for stimulating fibrinolysis and clot dissolution.

14. Method of claim 8 wherein said amount is about 5, 10, 20, 30 or 100 ng/mL and the relaxin or derivative thereof is in sterilized purified form.

15. Method of treating arteriosclerotic disease in a human patient exhibiting said disease, comprising administering to said patient in the absence of attendant exogenous estrogenic hormone an effective amount of relaxin or derivative thereof for relieving said disease.

16. Method of claim 15 wherein the disease involves increased concentration of lipids, cholesterol and triglycerides in the blood and the relaxin or derivative thereof is administered in an amount effective for controlling and reducing the concentration of lipids, cholesterol and triglycerides in the blood.

17. Method of claim 15 wherein said amount is about 5, 10, 20, 30 or 100 ng/mL and the relaxin or derivative thereof is in sterilized purified form.

18. Method of treating a condition of pre-eclampsia, eclampsia or gestosis of pregnancy in a human patient exhibiting said condition, comprising administering to said patient an effective amount of relaxin or derivative thereof for relieving said pre-eclampsia, eclampsia or gestosis of pregnancy.

19. Method of claim 18 wherein said amount is about 5, 10, 20, 30 or 100 ng/mL and the relaxin or derivative thereof is in sterilized purified form.

20. Method of a treating a condition deriving from the release of histamine involving allergic rhinitis, bronchial asthma, anaphylactic disease,
pharmacological allergy,
alteration in tissue reaction, or
inflammation sustained by the release of histamine, in a human patient exhibiting said condition, comprising administering to said patient an effective amount of relaxin or derivative thereof for preventing said release of histamine for relieving said rhinitis, for relieving said asthma, for relieving said anaphylactic disease, for relieving said pharmacological allergy, for relieving said alteration in tissue reaction, or for reducing or inhibiting said inflammation.

21. Method of claim 20 wherein the condition involves allergic rhinitis and the relaxin or derivative thereof is administered in an amount effective for relieving said rhinitis.

22. Method of claim 20 wherein the condition involves bronchial asthma and the relaxin or derivative thereof is administered in an amount effective for relieving said asthma.

23. Method of claim 20 wherein the condition involves anaphylactic disease and the relaxin or derivative thereof is administered in an amount effective for relieving said anaphylactic disease.

24. Method of claim 20 wherein the condition involves pharmacological allergy and the relaxin or derivative thereof is administered in an amount effective for relieving said pharmacological allergy.

25. Method of claim 20 wherein the condition involves alteration in tissue reaction and the relaxin or derivative thereof is administered in an amount effective for relieving said reaction.

26. Method of claim 25 wherein the alteration in tissue reaction is a skin rash and the relaxin or derivative thereof is administered in an amount effective for relieving said rash.

27. Method of claim 20 wherein the condition involves an inflammation sustained by the release of histamine and the relaxin or derivative thereof is administered in an amount effective for reducing or inhibiting said inflammation.

28. Method of claim 20 wherein said amount is about 5, 10, 20, 30 or 100 ng/mL and the relaxin or derivative thereof is in sterilized purified form.

29. Method of treating a condition selected from the group consisting of
circulatory vascular ischemic disease involving
constriction of the blood vessels,
vascular dysfunction, or
obliterative or obstructive peripheral arteriopathy;
circulatory thrombotic disease;
arteriosclerotic disease; and
a condition deriving from the release of histamine involving
allergic rhinitis,
bronchial asthma,
anaphylactic disease,
pharmacological allergy,
alteration in tissue reaction, or
inflammation sustained by the release of histamine; in a human patient exhibiting said condition by stimulating the synthesis and release of nitric oxide, NO, in said patient,
(a) comprising administering in the absence of attendant exogenous estrogenic hormone to said patient exhibiting said circulatory vascular ischemic disease, said circulatory thrombotic disease, and said arteriosclerotic disease, respectively, an effective amount of relaxin or derivative thereof for stimulating said synthesis and release of nitric oxide sufficiently for correspondingly relieving said circulatory vascular ischemic disease, relieving said circulatory thrombotic disease, and relieving said arteriosclerotic disease, and
(b) comprising administering to said patient exhibiting said condition deriving from the release of histamine an effective amount of relaxin or derivative thereof for stimulating said synthesis and release of nitric oxide sufficiently for treating said condition deriving from the release of histamine.

30. Method of claim 29 wherein said amount is about 5, 10, 20, 30 or 100 ng/mL and the relaxin or derivative thereof is in sterilized purified form.

31. Method of treating a condition selected from the group consisting of
circulatory vascular ischemic disease involving
constriction of the blood vessels,
vascular dysfunction, or
obliterative or obstructive peripheral arteriopathy; and
circulatory thrombotic disease;
in a human patient exhibiting said condition by stimulating the synthesis and release of nitric oxide, NO, in said patient, comprising administering in the absence of attendant exogenous estrogenic hormone to said patient an effective amount of relaxin or derivative thereof for stimulating said synthesis and release of nitric oxide sufficiently for correspondingly inducing vasodilation for relieving said circulatory vascular ischemic disease, and inhibiting blood coagulation for relieving said circulatory thrombotic disease.

32. Method of claim 31 wherein said amount is effective for intensifying fibrinolysis, inhibiting the aggregation of platelets and reducing the concentration of platelets in the blood.

33. Method of claim 31 wherein said amount is about 5, 10, 20, 30 or 100 ng/mL and the relaxin or derivative thereof is in sterilized purified form.

34. Method of treating a condition selected from the group consisting of
circulatory vascular ischemic disease involving
constriction of the blood vessels,
vascular dysfunction, or
obliterative or obstructive peripheral arteriopathy; and
circulatory thrombotic disease;
in a human patient exhibiting said condition by stimulating the synthesis and release of nitric oxide, NO, and the release of atrial natriuretic peptide, ANP, in said patient, comprising administering in the absence of attendant exogenous estrogenic hormone to said patient an effective amount of relaxin or derivative thereof for stimulating said synthesis and release of nitric oxide, and said release of atrial natriuretic peptide, sufficiently for correspondingly inducing vasodilation for relieving said circulatory vascular ischemic disease, and inhibiting blood coagulation for relieving said circulatory thrombotic disease.

35. Method of claim 34 wherein said amount is effective for intensifying fibrinolysis, inhibiting the aggregation of platelets and reducing the concentration of platelets in the blood.

36. Method of claim 34 wherein said amount is about 5, 10, 20, 30 or 100 ng/mL and the relaxin or derivative thereof is in sterilized purified form.

37. Method of treating circulatory thrombotic disease in a human patient exhibiting said disease, consisting essentially of administering to said patient an effective amount of relaxin or derivative thereof for relieving said disease.

* * * * *